(12) United States Patent
Petermann

(10) Patent No.: US 10,947,322 B2
(45) Date of Patent: Mar. 16, 2021

(54) ESTERIFIED CELLULOSE ETHERS COMPRISING PHTHALYL GROUPS

(71) Applicant: Dow Global Technologies LLC, Midland, MI (US)

(72) Inventor: Oliver Petermann, Hamburg (DE)

(73) Assignee: Nutrition & Biosciences USA 1, LLC, Rochester, NY (US)

( * ) Notice: Subject to any disclaimer, the term of this patent is extended or adjusted under 35 U.S.C. 154(b) by 0 days.

(21) Appl. No.: 16/072,650

(22) PCT Filed: Jun. 20, 2017

(86) PCT No.: PCT/US2017/038217
§ 371 (c)(1),
(2) Date: Jul. 25, 2018

(87) PCT Pub. No.: WO2017/233017
PCT Pub. Date: Dec. 28, 2017

(65) Prior Publication Data
US 2020/0010572 A1   Jan. 9, 2020

Related U.S. Application Data

(60) Provisional application No. 62/353,788, filed on Jun. 23, 2016.

(51) Int. Cl.
C08B 13/00 (2006.01)
A61K 47/38 (2006.01)
C08L 1/32 (2006.01)
A61K 9/10 (2006.01)
A61K 9/48 (2006.01)

(52) U.S. Cl.
CPC ............... *C08B 13/00* (2013.01); *A61K 9/10* (2013.01); *A61K 9/4816* (2013.01); *A61K 9/4833* (2013.01); *A61K 47/38* (2013.01); *C08L 1/32* (2013.01)

(58) Field of Classification Search
None
See application file for complete search history.

(56) References Cited

U.S. PATENT DOCUMENTS

| 3,629,237 A | 12/1971 | Koyanagi et al. |
| 4,287,221 A * | 9/1981 | Tonedachi ........... A61K 9/4891 424/459 |
| 2004/0152886 A1 * | 8/2004 | Cho ...................... C08B 13/00 536/66 |

FOREIGN PATENT DOCUMENTS

| EP | 0219426 | 4/1987 |
| EP | 2832372 | 2/2015 |
| WO | 2005074395 | 8/2005 |
| WO | 2006082518 | 8/2006 |
| WO | 2014137777 | 9/2014 |

* cited by examiner

*Primary Examiner* — Melissa S Mercier

(57) ABSTRACT

An esterified cellulose ether is provided wherein the ester groups are phthalyl groups, the degree of substitution of phthalyl groups is from 0.02 to 0.18, the degree of neutralization of phthalyl groups is not more than 0.75, and the esterified cellulose ether has a solubility in water of at least 2.0 weight percent at 2° C.

20 Claims, No Drawings

ESTERIFIED CELLULOSE ETHERS COMPRISING PHTHALYL GROUPS

FIELD

This invention concerns novel esterified cellulose ethers comprising phthalyl groups and their use for producing capsule shells or solid drug dispersions or for coating dosage forms.

INTRODUCTION

Various esterified cellulose ethers are useful in the pharmaceutical field, such as hydroxypropyl methyl cellulose phthalate (HPMCP). International Patent Application WO 2014/137777 discloses esterified cellulose ethers, such as HPMCP, of low viscosity in aqueous NaOH or acetone. International patent application WO 2006/082518 discloses HPMCP having a degree of substitution of phthalyl groups of 0.68.

U.S. Pat. No. 3,629,237 discloses acid phthalates of cellulose ethers, such as hydroxypropyl cellulose phthalate (HPCP), hydroxybutyl methylcellulose phthalate (HBMCP), hydroxypropyl methylcellulose phthalate (HPMCP), hydroxybutyl cellulose phthalate (HBCP), and hydroxypropyl ethylcellulose phthalate (HPECP). The U.S. patent discloses that these acid phthalates of cellulose ethers are soluble in organic solvents and useful as enteric coatings. Tablets coated with HPMCP compositions were insoluble in artificial gastric fluid but were decomposed in about 3 minutes in artificial intestinal fluid.

H. Kokubo et al. disclose "Development of Cellulose Derivatives as Novel Enteric Coating Agents Soluble at pH 3.5-4.5 and Higher" in Chem. Pharm. Bull. 45(8) 1350-1353 (1997), Vol. 45, No. 8. Hydroxypropyl methyl cellulose (HPMC) was selected as base polymer to develop novel enteric coating agents for acid protection which can dissolve at pH around 4. HPMC was modified with phthalic acid at various degrees of substitution. Enteric polymers are those that are resistant to dissolution in the acidic environment of the stomach. Dosage forms coated with such polymers protect the drug from inactivation or degradation in the acidic environment or prevent irritation of the stomach by the drug. As disclosed in the article of H. Kokubo et al., enteric coating polymers having carboxyl groups in their undissociated form have very low solubility in water. The degree of neutralization defines the ratio of deprotonated carboxylic groups over the sum of deprotonated and protonated carboxylic groups; i.e., the lower the degree of neutralization, the more carboxyl groups are present in their undissociated form. When the pH is raised by titration, the degree of neutralization of the carboxylic groups increases and water-solubility of the polymers increases. HPMCP grade HP-50 is insoluble in purified water when its degree of neutralization is less than 0.8.

HPMCP is commercially available from Shin-Etsu Chemical Co., Ltd as HPMCP grades HP-50, HP-55 and HP-55S. They have a nominal phthalyl content of 24% and 31%, which corresponds to a degree of substitution of phthalyl groups of 0.40 and 0.66 respectively, weight average molecular weights Mw of 78,000; 84,000; and 132,000 and a ratio of Mw/Mn of 3.3; 4.1; and 4.0, respectively. HPMCP grade HP-50 and HPMCP grade HP-55 are also commercially available from Samsung Fine Chemicals Co.; they are sold under the trademark being AnyCoat-P. The technical brochure discloses that AnyCoat-P HP-50 and HP-55 are not soluble in water and should be dissolved in an organic solvent to prepare an enteric coating.

European Patent Application EP 2 832 372 discloses compositions for enteric hard capsules comprising HPMCP grade HP-50, which contains 22.3 wt. % methoxy groups, 8.5 wt. % hydroxypropoxy groups, and 25.21 wt. % phthalyl groups. The production of the enteric hard capsules requires the presence of a water-soluble divalent base and an alkaline material. However, an excessive amount of neutralizing agent may gradually separate from the hardened capsules, also called a separation of salt.

International Patent Application WO 2005/074395 discusses that the use of HPMCP may cause environmental problems due to the use of an organic solvent for dissolving the HPMCP. WO 2005/074395 states that there is an increasing demand on the development of novel environment-friendly products and aqueous dispersions of PHMCP have been developed to meet this need. According to a conventional method HPMCP is completely dissolved in an organic solvent and then diffused in water. Then, the organic solvent is removed from the solution to obtain an aqueous dispersion of HPMCP. However, this method still provides disadvantages due to the use of organic solvents, such as high production costs and potentially remaining amounts of organic solvents in the HPMCP. WO 2005/074395 suggests the production of aqueous dispersions of HPMCP nanoparticle compositions. A neutralization-emulsification is conducted to produce the dispersion. Unfortunately, the production of the dispersion takes 2-4 hours at 40-60° C.

Accordingly, it would be desirable to find new types of esterified cellulose ethers which do not require the use of large quantities of organic solvents for dissolution or time-consuming processes for producing aqueous dispersions of the esterified cellulose ethers.

Surprisingly, novel esterified cellulose ethers comprising phthalyl groups have been found which can be dissolved in water although they comprise non-neutralized phthalyl groups. The preferred embodiments of these esterified cellulose ethers display resistance to dissolution in the acidic environment of the stomach.

SUMMARY

One aspect of the present invention is an esterified cellulose ether wherein the ester groups are phthalyl groups, the degree of substitution of phthalyl groups is from 0.02 to 0.18, the degree of neutralization of phthalyl groups is not more than 0.75, and the esterified cellulose ether has a solubility in water of at least 2.0 weight percent at 2° C.

Another aspect of the present invention is a liquid composition which comprises at least one above-described esterified cellulose ether dissolved an aqueous diluent.

Yet another aspect of the present invention is a liquid composition which comprises at least one above-described esterified cellulose ether and an organic diluent.

Yet another aspect of the present invention is a process for coating a dosage form which comprises the step of contacting an above-mentioned liquid composition with the dosage form.

Yet another aspect of the present invention is a process for the manufacture of capsule shells which comprises the step of contacting the above-mentioned liquid composition with dipping pins.

Yet another aspect of the present invention is a coated dosage form wherein the coating comprises at least one above-described esterified cellulose ether.

Yet another aspect of the present invention is a polymeric capsule shell which comprises at least one above-described esterified cellulose ether.

Yet another aspect of the present invention is a capsule which comprises the above-mentioned capsule shell and further comprises a drug or a nutritional or food supplement or a combination thereof.

Yet another aspect of the present invention is a solid dispersion of at least one active ingredient in at least one above-described esterified cellulose ether.

DESCRIPTION OF EMBODIMENTS

Surprisingly, it has been found that the esterified cellulose ethers of the present invention have a solubility in water of at least 2.0 weight percent at 2° C. Clear or turbid solutions with only a small portion of sediment or in the preferred embodiments even without sediment are obtained at a temperature of 2° C. or below. When the temperature of the prepared solution is increased to 15° C. or even to 20° C., no precipitation occurs. Moreover, aqueous solutions of the preferred embodiments of the esterified cellulose ether of the present invention gel at slightly elevated temperature. This renders the esterified cellulose ether of the present invention very useful in a variety of application, e.g. for producing capsules or for coating dosage forms. The advantages of the esterified cellulose ether of the present invention will be described in more detail below.

The esterified cellulose ether has a cellulose backbone having (3-1,4 glycosidically bound D-glucopyranose repeating units, designated as anhydroglucose units in the context of this invention. The esterified cellulose ether preferably is an esterified alkyl cellulose, esterified hydroxyalkyl cellulose or hydroxyalkyl alkylcellulose, more preferably an esterified hydroxyalkyl methylcellulose. This means that in the esterified cellulose ether of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as an esterified hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylation agent, e.g. a methylation agent, and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxy units are covalently bound to each other by ether bonding. Within this definition it is not important whether the terminal hydroxyl group of a hydroxyalkoxyl substituent is further alkylated, e.g. methylated, or not; both alkylated and non-alkylated hydroxyalkoxyl substituents are included for the determination of MS(hydroxyalkoxyl). The esterified cellulose ether of the invention generally has a molar substitution of hydroxyalkoxyl groups in the range 0.05 to 1.00, preferably 0.08 to 0.70, more preferably 0.15 to 0.60, most preferably 0.15 to 0.40, and particularly 0.20 to 0.40.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers according to this invention generally have a DS(alkoxyl) in the range of 1.0 to 2.5, preferably from 1.2 to 2.2, more preferably from 1.6 to 2.05, and most preferably from 1.7 to 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether of the present invention comprises phthalyl groups as ester groups. Specific examples of esterified cellulose ethers are hydroxypropyl methyl cellulose phthalates (HPMCP).

An essential feature of the esterified cellulose ethers of the present invention is their degree of substitution of phthalyl groups. The degree of substitution of phthalyl groups is at least 0.02, preferably at least 0.03, more preferably at least 0.04, and most preferably at least 0.05. The degree of substitution of phthalyl groups is not more than 0.18. In some embodiments of the invention the degree of substitution of phthalyl groups is up to 0.17 or up to 0.16. The esterified cellulose ethers of the present invention having a degree of substitution of phthalyl groups of from 0.02 to 0.15 have been found to gel at elevated temperatures as described in the Examples section, depending on their concentration in water.

The content of the phthalyl groups is determined according to Hypromellose phthalate, United States Pharmacopia and National Formulary, NF 33, pp. 6701-6702.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(\text{OCH}_3) - M(\text{OH})}{M(\text{OCH}_3)}\right) -$$
$$\left(\% \text{ HPO} * \frac{M(\text{OCH}_2\text{CH}(\text{OH})\text{CH}_3) - M(\text{OH})}{M(\text{OCH}_2\text{CH}(\text{OH})\text{CH}_3)}\right) -$$
$$\left(\% \text{ Phthalyl} * \frac{M(\text{COC}_6\text{H}_4\text{COOH}) - M(\text{H})}{M(\text{COC}_6\text{H}_4\text{COOH})}\right)$$

$$DS(Me) = \frac{\frac{\% \text{ MeO}}{M(\text{OCH}_3)}}{\frac{\% \text{ cellulose backbone}}{M(AGU)}}$$

$$MS(HP) = \frac{\frac{\% \text{ HPO}}{M(\text{HPO})}}{\frac{\% \text{ cellulose backbone}}{M(AGU)}}$$

$$DS(\text{Phthalyl}) = \frac{\frac{\% \text{ Phtalyl}}{M(\text{Phthalyl})}}{\frac{\% \text{ cellulose backbone}}{M(AGU)}}$$

$M(MeO) = M(\text{OCH}_3) = 31.03 \, Da$ $M(HPO) = M(\text{OCH}_2\text{CH}(\text{OH})\text{CH}_3) = 75.09 \, Da$ $M(\text{Phthalyl}) = M(\text{COC}_6\text{H}_4\text{COOH}) = 149.13 \, Da$ $M(AGU) = 162.14 \, Da$ $M(\text{OH}) = 17.008 \, Da$ $M(\text{H}) = 1.008 \, Da$ By convention, the weight percent is an average weight percentage based on the total weight of the cellulose repeat unit, including all substituents. The content of the methoxyl group is reported based on the mass of the methoxyl group (i.e., —$OCH_3$). The content of the hydroxyalkoxyl group is reported based on the mass of the hydroxyalkoxyl group (i.e., —O— alkylene-OH); such as hydroxypropoxyl (i.e., —O—$CH_2CH(CH_3)$—OH). The content of the phthalyl group is reported based on the mass of the phthalyl group (i.e., —C(O)—$C_6H_4$—COOH).

The esterified cellulose ethers of the present invention generally have a weight average molecular weight $M_w$ of up to 500,000 Dalton, preferably up to 200,000 Dalton, more preferably up to 150,000 Dalton, and most preferably up to 100,000 Dalton or up to 50,000 Dalton. Generally they have a weight average molecular weight $M_w$ of at least 10,000 Dalton, preferably at least 15,000 Dalton, more preferably at least 20,000 Dalton, and most preferably at least 25,000 Dalton.

The esterified cellulose ethers of the present invention generally have a Polydispersity $M_w/M_n$, i.e., a ratio of weight average molecular weight $M_w$ to number average molecular weight $M_n$, of at least 1.2, typically at least 1.3. Moreover, the esterified cellulose ethers of the present invention generally have a Polydispersity of up to 2.6, preferably of up to 2.3, more preferably of up to 1.9, and most preferably up to 1.6.

$M_w$ and $M_n$ are measured according to Journal of Pharmaceutical and Biomedical Analysis 56 (2011) 743 using a mixture of 40 parts by volume of acetonitrile and 60 parts by volume of aqueous buffer containing 50 mM $NaH_2PO_4$ and 0.1 M $NaNO_3$ as mobile phase. The mobile phase is adjusted to a pH of 8.0.

In the esterified cellulose ether of the present invention the degree of neutralization of the phthalyl groups is not more than 0.75, generally not more than 0.6, preferably not more than 0.5, more preferably not more than 0.3, most preferably not more than 0.1, and particularly not more than 0.05 or even not more than 0.01. The degree of neutralization can even be essentially zero or only slightly above it, e.g. up to $10^{-3}$ or even only up to $10^{-4}$. The term "degree of neutralization" as used herein defines the ratio of deprotonated carboxylic groups over the sum of deprotonated and protonated carboxylic groups, i.e., degree of neutralization= [—C(O)—$C_6H_4$—COO$^-$]/[—C(O)—$C_6H_4$—COO$^-$+—C(O)—$C_6H_4$—COOH].

The degree of neutralization can be evaluated by titration as described by H. Kokubo et al. in "Development of Cellulose Derivatives as Novel Enteric Coating Agents Soluble at pH 3.5-4.5 and Higher" in *Chem. Pharm. Bull.* 45(8) 1350-1353 (1997), Vol. 45, No. 8, at page 1350. In neutralized phthalyl groups the counter-cations preferably are ammonium cations, such as $NH_4^+$, or alkali metal ions, such as sodium or potassium ions, more preferably sodium ions.

Another essential property of the esterified cellulose ether of the present invention is its water-solubility. Surprisingly, the esterified cellulose ether of the present invention has a solubility in water of at least 2.0 weight percent at 2° C., i.e., it can be dissolved as an at least 2.0 weight percent solution, preferably at least 3.0 weight percent solution, more preferably at least 5.0 weight percent solution, and most preferably even at least 10.0 weight percent solution in water at 2° C. Generally the esterified cellulose ether of the present invention can be dissolved as up to 20 weight percent solution or in the most preferred embodiments even as up to 30 weight percent solution in water at a temperature of 2° C. The term "an x weight percent solution in water at 2° C." as used herein means that x g of the esterified cellulose ether is soluble in (100−x) g of water at 2° C.

When determining the water solubility as described in the Examples section, the esterified cellulose ether of the present invention preferably has solubility properties that at least 85 wt. %, typically at least 90 wt. %, more typically at least 95 wt. %, and in many cases at least 99 wt. % of the esterified cellulose ether is soluble in a mixture of 2.5 weight parts of the esterified cellulose ether and 97.5 weight parts of water at 2° C. Typically this degree of solubility is also observed in a mixture of 5 or 10 weight parts of the esterified cellulose ether and 95 or 90 weight parts of water at 2° C. or even in a mixture of 20 weight parts of the esterified cellulose ether and 80 weight parts of water at 2° C.

In more general terms, it has surprisingly been found that the esterified cellulose ether of the present invention, in spite of its low degree of neutralization of phthalyl groups, is soluble in an aqueous liquid at a temperature of 2° C., even when the esterified cellulose ether is blended with an aqueous liquid that does not increase the degree of neutralization of the esterified cellulose ether to more than 0.75 or a preferred range listed above, e.g., when the esterified cellulose ether is blended with only water, such as deionized or distilled water. Clear or turbid solutions without sediment are obtained at 2° C.

Moreover, it has been found that aqueous solutions of an esterified cellulose ether of the present invention having a degree of substitution of ester groups of from 0.02 to 0.15 gel at elevated temperature, typically at 50 to 90° C., more typically at 60 to 80° C. This renders this embodiment of the esterified cellulose ether of the present invention very useful in a variety of application, e.g. for producing capsules and for coating dosage forms. Gelling of aqueous solutions of these esterified cellulose ethers, such as hydroxypropyl methyl cellulose phthalates (HPMCP), at elevated temperature is observed even when aqueous solutions of the cellulose ethers that are used as starting materials for producing the esterified cellulose ethers do not gel. E.g., the Examples of the present invention illustrate gelling HPMCP of the present invention, although the corresponding hydroxypropyl methyl cellulose that is used as a starting material for preparing them does not gel to a significant degree. Gelation of the esterified cellulose ethers of the present invention typically occurs at concentrations of 2 to 30 weight percent, more typically at 5 to 20 weight percent, based on the total weight of esterified cellulose ether and aqueous liquid. The gelation is reversible, i.e. upon cooling to 20° C. the gel transforms into a liquid aqueous solution.

The aqueous liquid in which the esterified cellulose ether of the present invention is soluble may additionally comprise a minor amount of an organic liquid diluent; however, the aqueous liquid should generally comprise at least 80, preferably at least 85, more preferably at least at least 90, and particularly at least 95 weight percent of water, based on the total weight of the aqueous liquid. The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran; acetates, such as ethyl acetate; halogenated hydrocarbons, such as methylene chloride; or nitriles, such as acetonitrile. More preferably the organic liquid diluents have 1 to 6, most preferably 1 to 4 carbon atoms. The aqueous liquid may comprise a basic compound, but the degree of neutralization of the phthalyl groups of the esterified cellulose ether in the resulting blend of esterified cellulose ether and aqueous liquid should not be more than 0.75 or a preferred upper limit as described further above. Preferably the aqueous liquid does not comprise a substantial amount of a basic compound. More preferably, the aqueous diluent does not contain a basic compound. Even more preferably, the aqueous liquid comprises from 80 to 100 percent, preferably 85 to 100 percent, more preferably 90 to 100 percent and most preferably 95 to 100 percent of water, and from 0 to 20 percent, preferably 0 to 15 percent, more preferably 0 to 10 percent, and most preferably 0 to 5 percent of an organic liquid diluent, based on the total weight of the aqueous liquid. Most preferably the aqueous liquid consists of water, e.g., deionized or distilled water.

The esterified cellulose ethers of the present invention generally have a viscosity of up to 200 mPa·s, preferably up to 100 mPa·s, more preferably up to 50 mPa·s, and most preferably up to 5.0 mPa·s, measured as a 2.0 wt.-% solution of the esterified cellulose ether in 0.43 wt.-% aqueous NaOH at 20° C. Generally the viscosity is at least 1.2 mPa·s, more typically at least 1.8 mPa·s, even more typically at least 2.4 mPa·s, and most typically at least 2.8 mPa·s, measured as a 2.0 wt.-% solution of the esterified cellulose ether in 0.43 wt.-% aqueous NaOH at 20° C.

Details of the production of the esterified cellulose ethers of the present invention are described in the examples. Some aspects of the production process are described below. The esterified cellulose ether of the present invention can be produced by esterifying a cellulose ether, such as an alkyl cellulose, hydroxyalkyl cellulose or hydroxyalkyl alkylcellulose described further above. The cellulose ethers preferably have a DS(alkoxyl) and/or an MS(hydroxyalkoxyl) as described further above. The cellulose ether used as a starting material for esterification generally has a viscosity of from 1.2 to 200 mPa·s, preferably from 1.8 to 100 mPa·s, more preferably from 2.4 to 50 mPa·s and in particular from 2.8 to 5.0 mPa·s, measured as a 2 weight-% aqueous solution at 20° C. according to ASTM D2363-79 (Reapproved 2006). Cellulose ethers of such viscosity can be obtained by subjecting a cellulose ether of higher viscosity to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent.

The cellulose ether is reacted with phthalic anhydride. The molar ratio between the phthalic anhydride and the anhydroglucose units of cellulose ether generally is at least 0.02:1, preferably at least 0.05:1, more preferably at least 0.1:1, and even more preferably at least 0.12:1. In some embodiments of the invention, the molar ratio between the phthalic anhydride and the anhydroglucose units of cellulose ether is 0.15:1 or more or even 0.20:1 or more. The molar ratio between the phthalic anhydride and the anhydroglucose units of cellulose ether generally is not more than 0.45:1, typically not more than 0.44:1, and more typically not more than 0.43:1. The molar number of anhydroglucose units of the cellulose ether utilized in the process can be determined from the weight of the cellulose ether used as a starting material, by calculating the average molecular weight of the substituted anhydroglucose units from the DS(alkoxyl) and MS(hydroxyalkoxyl).

The esterification of the cellulose ether is conducted in an aliphatic carboxylic acid as a reaction diluent, such as acetic acid, propionic acid, or butyric acid. The reaction diluent can comprise minor amounts of other solvents or diluents which are liquid at room temperature and do not react with the cellulose ether, such as aromatic or aliphatic solvents like benzene, toluene, 1,4-dioxane, or tetrahydrofurane; or halogenated $C_1$-$C_3$ derivatives, like dichloro methane or dichloro methyl ether, but the amount of the aliphatic carboxylic acid should generally be more than 50 percent, preferably at least 75 percent, and more preferably at least 90 percent, based on the total weight of the reaction diluent. Most preferably the reaction diluent consists of an aliphatic carboxylic acid, more preferably acetic acid. The molar ratio [aliphatic carboxylic acid/anhydroglucose units of cellulose ether] generally is from 9.5:1 to 11:1, preferably from 10.0:1 to 10.5:1.

The esterification reaction is conducted in the presence of an esterification catalyst, preferably in the presence of an alkali metal carboxylate, such as sodium acetate or potassium acetate. The molar ratio [alkali metal carboxylate/anhydroglucose units of cellulose ether] is generally from [2.0/1.0] to [3.0/1.0], and preferably from [2.3/1.0] to [2.6/1.0].

The reaction temperature for the esterification is generally from 75° C. to 95° C., preferably from 80° C. to 90° C. The esterification reaction is typically completed within 2.5 to 4 hours. After completion of the esterification reaction, the esterified cellulose ether can be precipitated from the reaction mixture in a known manner, for example as described in U.S. Pat. No. 4,226,981, International Patent Application WO 2005/115330, European Patent Application EP 0 219 426 or International Patent Application WO2013/148154. The precipitated esterified cellulose ether is typically washed with an aqueous liquid at a temperature of from 70 to 100° C. Suitable aqueous liquids are described further above.

Another aspect of the present invention is an aqueous composition comprising one or more of the above described esterified cellulose ethers of the present invention dissolved in an aqueous liquid. The aqueous liquid is a described further above. The esterified cellulose ether of the present invention can be brought into aqueous solution by cooling the aqueous composition to a temperature of −2° C. to less than 10° C., preferably of 0° C. to less than 8° C., more preferably of 0.5° C. to less than 5° C., and most preferably of 0.5° C. to 3° C. The aqueous composition preferably comprises at least 5 wt.-%, more preferably at least 10 wt.-%, and preferably up to 30 wt.-%, more preferably up to 20 wt.-% of the esterified cellulose ether of the present invention, based on the total weight of the aqueous composition.

The aqueous composition comprising one or more of the above described esterified cellulose ethers of the present invention dissolved in an aqueous liquid is useful in the manufacture of capsules which comprises the step of contacting the liquid composition with dipping pins. Typically an aqueous composition having a temperature of less than 20° C., more typically less than 15° C. or in some embodiments less than 10° C. is contacted with dipping pins having a higher temperature than the aqueous composition and that have a temperature of at least 21° C., more typically at least 25° C., and up to 95° C., preferably up to 80° C.

The aqueous composition comprising one or more of the above described esterified cellulose ethers dissolved in an aqueous liquid is also useful for coating dosage forms, such as tablets, granules, pellets, caplets, lozenges, suppositories, pessaries or implantable dosage forms.

Another aspect of the present invention is a liquid composition comprising an organic diluent and one or more of the above described esterified cellulose ethers of the present invention. The organic diluent may be present in the liquid composition alone or mixed with water. Preferred organic diluents are described further above. The liquid composition preferably comprises at least 5 wt.-%, more preferably at least 10 wt.-%, and preferably up to 30 wt.-%, more preferably up to 20 wt.-% of the esterified cellulose ether of the present invention, based on the total weight of the liquid composition.

The composition of the present invention comprising an aqueous liquid or an organic diluent as described above and one or more of the above described esterified cellulose ethers is also useful as an excipient system for active ingredients and particularly useful as an intermediate for preparing an excipient system for active ingredients, such as fertilizers, herbicides or pesticides, or biologically active ingredients, such as vitamins, herbals and mineral supplements or drugs. Accordingly, the composition of the present invention preferably comprises one or more active ingredients, most preferably one or more drugs. The term "drug" is conventional, denoting a compound having beneficial prophylactic and/or therapeutic properties when administered to an animal, especially humans. In another aspect of the invention the composition of the present invention is used for producing a solid dispersion comprising at least one active ingredient, such as a drug, at least one esterified cellulose ether as described above and optionally one or more adjuvants. A preferred method of producing a solid dispersion is by spray-drying. Spray-drying processes and spray-drying equipment are described generally in Perry's Chemical Engineers' Handbook, pages 20-54 to 20-57 (Sixth Edition 1984). Alternatively, the solid dispersion of the present invention may be prepared by i) blending a) at least one esterified cellulose ether defined above, b) one or more active ingredients and c) one or more optional additives, and ii) subjecting the blend to extrusion. The term "extrusion" as used herein includes processes known as injection molding, melt casting and compression molding. Techniques for extruding, preferably melt-extruding compositions comprising an active ingredient such as a drug are known and described by Joerg Breitenbach, Melt extrusion: from process to drug delivery technology, European Journal of Pharmaceutics and Biopharmaceutics 54 (2002) 107-117 or in European Patent Application EP 0 872 233. The solid dispersion of the present invention preferably comprises a) from 20 to 99.9 percent, more preferably from 30 to 98 percent, and most preferably from 60 to 95 percent of an esterified cellulose ether as described above, and b) preferably from 0.1 to 80 percent, more preferably from 2 to 70 percent, and most preferably from 5 to 40 percent of an active ingredient b), based on the total weight of the esterified cellulose ether a) and the active ingredient b). The combined amount of the esterified cellulose ether a) and the active ingredient b) is preferably at least 70 percent, more preferably at least 80 percent, and most preferably at least 90 percent, based on the total weight of the solid dispersion. The remaining amount, if any, consists of one or more of the adjuvants c) as described below. Once the solid dispersion comprising at least one active ingredient in at least one esterified cellulose ether has been formed, several processing operations can be used, such as drying, granulation, and milling, to facilitate incorporation of the dispersion into a dosage form, such as strands, pellets, granules, pills, tablets, caplets, microparticles, fillings of capsules or injection molded capsules or in the form of a powder, film, paste, cream, suspension or slurry.

The aqueous composition, the liquid composition comprising an organic diluent and the solid dispersion of the present invention may further comprise optional adjuvants, such as coloring agents, pigments, opacifiers, flavor and taste improvers, antioxidants, and any combination thereof.

Some embodiments of the invention will now be described in detail in the following Examples.

EXAMPLES

Unless otherwise mentioned, all parts and percentages are by weight. In the Examples the following test procedures are used.

Content of Ether and Ester Groups

The content of ether groups in the esterified cellulose ether is determined in the same manner as described for "Hypromellose", United States Pharmacopeia and National Formulary, USP 35, pp 3467-3469.

The content of the phthalyl groups is determined according to Hypromellose phthalate, United States Pharmacopia and National Formulary, NF 33, pp. 6701-6702.

Water-Solubility

Quantitative Determination:

2.5 weight parts of HPMCP, based on its dry weight, were added to 97.5 weight parts of deionized water having a temperature of 2° C. followed by stirring for 6 hours at 2° C. and storing for 16 h at 2° C. A weighed amount of this mixture was transferred to a weighed centrifuge vial; the transferred weight of the mixture was noted as M1 in g. The transferred weight of HPMCP [M2] was calculated as (transferred weight of mixture in g/100 g×2.5 g). The mixture was centrifuged for 60 min at 5000 rpm (2823×g, Biofuge Stratos centrifuge from Thermo Scientific) at 2° C. After centrifugation an aliquot was removed from the liquid phase and transferred to a dried weighed vial. The weight of the transferred aliquot was recorded as M3 in g. The aliquot was dried at 105° C. for 12 h. The remaining g of HPMCP was weighed after drying and recorded as M4 in g.

The term "% water soluble at 2.5%" in Table 2 below expresses the percentage of HPMCP that is actually dissolved in the mixture of 2.5 weight parts of HPMCP and 97.5 weight parts of deionized water. It is calculated as (M4/M2)×(M1/M3)×100, which corresponds to
(g HPMCP in liquid aliquot/g HPMCP transferred to centrifuge vial)×(g mixture transferred to centrifuge vial/g liquid aliquot after centrifugation)×100. In the formulas above "×" stands for the multiplication operator.

Qualitative Determination:

A 2 wt. percent mixture of HPMCP and water was prepared by mixing 2.0 g HPMCP, based on its dry weight, with 98.0 g water under vigorous stirring at 0.5° C. for 16 hours. The temperature of the mixture of HPMCP and water was then increased to 4° C. in a refrigerator. HPMCP that is soluble at 4° C. is also soluble at 2° C.; at 2° C. the solubility is at least as high as at 4° C. The water solubility of the HPMCP was determined by visual inspection. The determination whether the HPMCP was water-soluble at 2% at 2° C. or not was done as follows. "Water soluble at 2%—yes" means that a solution without sediment was obtained according to the procedure above. "Water soluble at 2%—no" means that at least a significant portion of the HPMCP remained undissolved and formed sediment when mixing 2.0 g HPMCP, based on its dry weight, with 98.0 g water according to the procedure above. "Water soluble at 2%—partially" means that only a small portion of the HPMCP remained undissolved and formed sediment when mixing 2.0 g HPMCP, based on its dry weight, with 98.0 g water according to the procedure above.

Viscosity of Hydroxypropyl Methyl Cellulose Phthalate (HPMCP)

The 2.0% by weight solution of the HPMCP in 0.43 wt. % aqueous NaOH was prepared as described in "Hypromellose Phthalate, United States Pharmacopia and National Formulary, NF. An Ubbelohde viscosity measurement according to DIN 51562-1:1999-01 (January 1999) was carried out. The measurement was done at 20° C. The 2.0% by weight solution of the HPMCP in 0.43 wt. % aqueous NaOH is listed in Table 2 below as "2.0% viscosity in 0.43% NaOH".

The 10 wt.-% solution of HPMCP in a 1:1 by weight mixture of dichloromethane and methanol was prepared by mixing 10.0 g HPMCP, with 45.0 g of dichloromethane and 45.0 g of methanol under vigorous stirring at room temperature. The mixture was rolled on a roller mixer for about 24 hours. The solution was centrifuged at 2000 rpm for 3 minutes using a Megafuge 1.0 centrifuge, commercially available from Heraeus Holding GmbH, Germany. An Ubbelohde viscosity measurement according to DIN 51562-1:1999-01 (January 1999) was carried out. The measurement was done at 20° C.

Gelation Temperature and Gel Strength of Solutions of HPMCP in Water

A 2 wt.-%, 5 wt.-% or 10 wt.-% solution of HPMCP in water was produced by adding a corresponding amount of milled, ground, and dried HPMCP (under consideration of the water content of the HPMCP) to water (temperature 20-25° C.) at room temperature while stirring with an overhead lab stirrer at 750 rpm with a 3-wing (wing=2 cm) blade stirrer. The solution was then cooled to about 1.5° C. After the temperature of 1.5° C. was reached the solution was stirred for 120 min at 500 rpms. Each solution was stored in the refrigerator prior to the characterization.

Rheology measurements of the HPMCP solutions in water were conducted with a Haake RS600 (Thermo Fisher Scientific) rheometer with cup and bob fixtures (CC-25). The samples were heated at a rate of 1° C. per minute over a temperature range from 5 to 85° C. with a constant strain (deformation) of 2% and a constant angular frequency of 2 Hz. The measurement collection rate was chosen to be 4 data points/min. The storage modulus G', which was obtained from the rheology measurements, represents the elastic properties of the solution and represents the gel strength in the high temperature region, when the storage modulus G' is higher than the loss modulus G".

The obtained data of the storage modulus G', which was obtained from the oscillation measurements, was first logarithmized and normalized to G' (min) to zero and G' (max) to 100. Linear regression curves were fitted to subsets of these storage modulus data (increments of 5 data points). A tangent was fitted to the steepest slope of the regression curve. The intersection of this tangent with the x-axis is reported as gelation temperature. Details how to determine the gelation temperature are described in International Patent Application WO2015/009796 on pages 18 and 19 in the paragraphs "Determination of the gelation temperature of aqueous compositions comprising methyl cellulose".

The gel strength according to the storage modulus G' at 65° C. was also obtained by this rheology measurement.

Production of HPMCP of Examples 1-5 and Comparative Examples A-E 700.0 g of acetic acid was filled in a reactor and stirred. Then 230.0 g of sodium acetate (water free) and 230.0 g of HPMC (water free) were added. The HPMC had a methoxyl substitution ($DS_M$) of 1.98, a hydroxypropoxyl substitution ($MS_{HP}$) of 0.25 and a viscosity of 3.0 mPa·s, measured as a 2% solution in water at 20° C. according to ASTM D2363-79 (Reapproved 2006). The weight average molecular weight of the HPMC was about 20,000 Dalton. The HPMC is commercially available from The Dow Chemical Company as Methocel E3 LV Premium cellulose ether. Inertisation with nitrogen was carried out. The mixture was heated to 85° C. under stirring. After reaching the temperature of 85° C. the reaction mixture was allowed to stir for 10 min. Then phthalic anhydride as listed in Table 1 below was added, and the reaction mixture was allowed to react for 3.5 hours. After the esterification reaction the mixture was quenched with 318.46 g of deionized water having a temperature of 50° C. Then 2 L of deionized water (temperature 50° C.) was added into the reactor under stirring to precipitate the HPMCP. The precipitated HPMCP cooled down to about 50° C. and was removed from the reactor. The HPMCP was washed twice with 1.7 L of hot water (temperature about 95°) by applying high shear mixing using an Ultra-Turrax stirrer S50-G45 running at 5000 rpm for 60 seconds. After filtration the filter cake was washed several times with 1.7 L of hot water. The washed HPMCP was isolated by vacuum-filtration and dried at 55° C. overnight.

TABLE 1

| (Comp.) Example | HPMC g | HPMC Mol | Glacial acetic acid g | Glacial acetic acid mol/mol HPMC | Phthalic anhydride g | Phthalic anhydride mol/mol HPMC | Sodium acetate g | Sodium acetate mol/mol HPMC |
|---|---|---|---|---|---|---|---|---|
| 1 | 230 | 1.14 | 700 | 10.3 | 20.0 | 0.12 | 230 | 2.46 |
| 2 | 230 | 1.14 | 700 | 10.3 | 40.0 | 0.24 | 230 | 2.46 |
| 3 | 230 | 1.14 | 700 | 10.3 | 60.0 | 0.36 | 230 | 2.46 |
| 4 | 230 | 1.14 | 700 | 10.3 | 65.0 | 0.38 | 230 | 2.46 |
| 5 | 230 | 1.14 | 700 | 10.3 | 70.0 | 0.41 | 230 | 2.46 |
| A | 230 | 1.14 | 700 | 10.3 | 75.0 | 0.44 | 230 | 2.46 |
| B | 230 | 1.14 | 700 | 10.3 | 80.0 | 0.47 | 230 | 2.46 |
| C | 230 | 1.14 | 700 | 10.3 | 100.0 | 0.59 | 230 | 2.46 |
| D | 230 | 1.14 | 700 | 10.3 | 120.0 | 0.71 | 230 | 2.46 |
| E | 230 | 1.14 | 700 | 10.3 | 140.0 | 0.82 | 230 | 2.46 |

The properties of the HPMCP of Examples 1-5 and Comparative Examples A-E are listed in Table 2 below. In Table 2 the abbreviations have the following meanings: $DS_M$=DS(methoxyl): degree of substitution of methoxyl groups; $MS_{HP}$=MS(hydroxypropoxyl): molar substitution of hydroxypropoxyl groups; $DS_{Ph}$: degree of substitution of phthalyl groups.

The results in Table 2 below illustrate that the esterified cellulose ethers of Examples 1-5 are soluble in water, but those of Comparative Examples A-E are not or insufficiently soluble in water. Moreover, esterified cellulose ethers of Examples 1-5 are soluble in some polar solvents, such as a mixture of dicloromethane and methanol. Even at 10 wt.-% solution the viscosity is low, similar to that of Comparative Examples A-E.

The esterified cellulose ether of Example 1 was soluble at a concentration of 2 wt.-% in water not only at a temperature of 2-4° C. but also at a temperature of 21° C.

Rheology measurements were carried out to measure the gelation temperatures and gel strength according to the storage modulus G' at 65° C. of 2 wt.-%, 5 wt.-% and/or 10 wt.-% solutions of the HPMCP of Examples 1, 2 or 3 in water as described further above. The results are listed in Table 3 below.

TABLE 3

| Example | Wt.-% HPMCP in water | Gelation Temperature, ° C. | Gel Strength G' at 65° C., Pa |
|---|---|---|---|
| 1 | 2 | 53 | 8 |
| 1 | 5 | 47 | 564 |
| 2 | 2 | — | — |
| 2 | 5 | 39 | 1330 |
| 2 | 10 | 30 | 8495 |

TABLE 2

| (Comparative) Example | Methoxyl (%) | Hydroxypropoxyl (%) | Phthalyl (%) | $DS_M$ | $MS_{HP}$ | $DS_{PH}$ | % water - soluble at 2.5% (quantitative) | Water-soluble at 2% (qualitative) | 2% viscosity in 0.43% NaOH [mPa·s] | Viscosity 10 wt.-% sol. in 1:1 dichloromethane/methanol (mPa·s) |
|---|---|---|---|---|---|---|---|---|---|---|
| 1 | 29.1 | 8.8 | 3.7 | 1.99 | 0.25 | 0.05 | 99 | Yes [1] | 4.27 | 80.7 |
| 2 | 28.1 | 8.5 | 7.0 | 1.99 | 0.25 | 0.10 | 98 | Yes [1] | 3.93 | 64.8 |
| 3 | 27 | 8.4 | 10.1 | 1.98 | 0.25 | 0.15 | 96 | Yes [2] | 3.63 | 52.1 |
| 4 | 26.9 | 8.4 | 10.5 | 1.98 | 0.26 | 0.16 | 99 | Yes [2] | 3.61 | 51.8 |
| 5 | 26.8 | 8.3 | 11.2 | 1.99 | 0.26 | 0.17 | 93 | Yes [2] | 3.53 | 48.9 |
| A | 26.5 | 8.2 | 12.0 | 1.99 | 0.25 | 0.19 | 67 | turbid solution, very little sediment | 3.53 | 48.1 |
| B | 26 | 8.1 | 13.5 | 1.98 | 0.26 | 0.21 | 53 | Partially [3] | 3.43 | 44.6 |
| C | 25.1 | 7.8 | 16.2 | 1.97 | 0.25 | 0.27 | 28 | Partially [3] | 3.27 | 38.7 |
| D | 24.1 | 7.6 | 19.7 | 1.98 | 0.26 | 0.34 | 11 | Partially [3] | 3.15 | 34.0 |
| E | 23 | 7.2 | 23.2 | 1.98 | 0.26 | 0.41 | 1 | No; sediment formed | 3.01 | 29.4 |

[1] clear solution
[2] slightly turbid
[3] sediment formed

Gelation

Some aqueous solutions of the HPMCP of the present invention gel at elevated temperature, typically at 45 to 90° C., more typically at 50 to 80° C. Preferred embodiments of the HPMCP of the present invention even gel at a concentration as low as 2 wt.-%. It is very surprising that the esterified hydroxyalkyl alkyl celluloses gel in spite of their very low total degree of ester substitution. The HPMC that is used as starting material for preparing the HPMCP does not gel at a concentration of 2 wt.-%. A 2 wt.-% solution of Methocel E3 LV Premium cellulose ether in water after heating to 65° C. does not form a gel but only flocculates.

TABLE 3-continued

| Example | Wt.-% HPMCP in water | Gelation Temperature, ° C. | Gel Strength G' at 65° C., Pa |
|---|---|---|---|
| 3 | 2 | — | — |
| 3 | 5 | 39 | 235 |
| Methocel E3 LV Premium cellulose ether | 2 | 55 | 0.6 * |
| | 5 | 63 | 2 |
| | 10 | 58 | 73 |

* No significant gelling, only flocculation

Enteric Properties of the HPMCP

Preparation of Capsules from HPMCP of Example 2

An aqueous solution of 15 wt.-% of the water soluble HPMCP obtained according to the procedure in Example 2 was prepared by dissolving the HPMCP in deionized water at a temperature of 2° C. Then 20 wt.-% of triethyl citrate (TEC), based on the weight of HPMCP was added to the aqueous solution. Capsule shells were produced by dipping metallic pins having room temperature (21° C.) into the aqueous HPMCP solution having a temperature of 18° C. The pins were then withdrawn from the aqueous HPMCP solution and a film formed on the molding pins. The capsule shells were dried at room temperature. The final thickness of the capsule shells was 50-140 μm.

Preparation of Capsules from HPMCP of Example 3

An aqueous solution of 17 wt.-% of the water soluble HPMCP obtained according to the procedure in Example 3 was prepared by dissolving the HPMCP in deionized water at a temperature of 4° C. Then 20 wt.-% of triethyl citrate (TEC), based on the weight of HPMCP was added to the aqueous solution. Capsule shells were produced by dipping metallic pins having a temperature of 30° C. into the aqueous solution having a temperature of 4° C. The pins were then withdrawn from the aqueous HPMCP solution and a film formed on the molding pins. The capsule shells were dried at room temperature. The final thickness of the capsule shells was about 45-110 μm.

To test the solubility of the capsule shells prepared from the HPMCP of Examples 2 and 3 in the acidic environment of the stomach, the capsule shells were broken into pieces and immersed into 0.1 N HCl. The capsule pieces were left there for 2 hours at a temperature of 37° C. to simulate the stomach fluid. The capsule pieces prepared from the HPMCP of Examples 2 and 3 did not dissolve in 0.1 N HCl during these 2 hours.

To test the solubility of the capsule shells in the intestine or colon, the 0.1 N HCl was poured off from the capsule pieces and the capsule pieces were then immersed into buffer solutions specified below.

Some capsule pieces were immersed for 2 hours into McIlvaine's buffer solutions (containing disodium monophosphate and citric acid) that had a temperature of 37° C. and a pH of 4.0; 4.5; 5.0; 5.5; 6.0 or 6.8, respectively. The capsule pieces prepared from the HPMCP of Examples 2 and 3 did not dissolve in the McIlvaine's buffer solution that had a pH of 4.0 but dissolved in McIlvaine's buffer solutions that had a pH of 4.5; 5.0; 5.5; 6.0 or 6.8, respectively.

Other capsule pieces were immersed for 2 hours into aqueous phosphate buffers of 0.2 M tribasic sodium phosphate that had a temperature of 37° C. and a pH of 5.5; 5.8; 6.0; 6.5 or 6.8, respectively. All capsule pieces prepared from the capsules of Examples 2 and 3 dissolved in the phosphate buffers.

The invention claimed is:

1. A hydroxypropyl methyl cellulose phthalate, wherein the degree of substitution of phthalyl groups is from 0.02 to 0.18, the degree of neutralization of phthalyl groups is not more than 0.75, wherein the degree of neutralization=[—C(O)—$C_6H_4$—COO$^-$]/[—C(O)—$C_6H_4$—COO$^-$+—C(O)—$C_6H_4$—COOH], and the hydroxypropyl methyl cellulose phthalate has a solubility in water of at least 2.0 weight percent at 2° C.

2. The hydroxypropyl methyl cellulose phthalate of claim 1 wherein the degree of substitution of phthalyl groups is from 0.05 to 0.17.

3. The hydroxypropyl methyl cellulose phthalate of claim 1 wherein the degree of neutralization of phthalyl groups is not more than 0.6.

4. The hydroxypropyl methyl cellulose phthalate of claim 1 wherein at least 85 wt. % of the hydroxypropyl methyl cellulose phthalate is soluble in a mixture of 2.5 weight parts of the hydroxypropyl methyl cellulose phthalate and 97.5 weight parts of water at 2° C.

5. A liquid composition comprising the hydroxypropyl methyl cellulose phthalate of claim 1 dissolved in an aqueous liquid.

6. The liquid composition of claim 5 having a temperature of 15° C. or less.

7. A liquid composition comprising at least one hydroxypropyl methyl cellulose phthalate of claim 1 and an organic diluent.

8. A process for coating a dosage form comprising contacting a liquid composition comprising the hydroxypropyl methyl cellulose phthalate of claim 1 with the dosage form.

9. A process for a manufacture of capsule shells comprising contacting a liquid composition comprising the hydroxypropyl methyl cellulose phthalate of claim 1 with dipping pins.

10. A coated dosage form wherein the coating comprises at least one hydroxypropyl methyl cellulose phthalate of claim 1.

11. A polymeric capsule shell comprising at least one hydroxypropyl methyl cellulose phthalate of claim 1.

12. A capsule comprising the polymeric capsule shell of claim 11 and an ingredient selected from the group consisting of a drug, a nutritional or food supplement, or a combination thereof.

13. A solid dispersion of at least one active ingredient in at least one hydroxypropyl methyl cellulose phthalate of claim 1.

14. The liquid composition of claim 5 wherein the hydroxypropyl methyl cellulose phthalate has the degree of substitution of phthalyl groups of from 0.02 to 0.15.

15. The liquid composition of claim 14, characterized in that the hydroxypropyl methyl cellulose phthalate gels at 50 to 90° C.

16. The liquid composition of claim 15 wherein the gelation is reversible.

17. The liquid composition of claim 5 wherein the liquid composition comprises at least 5 wt. % of the hydroxypropyl methyl cellulose phthalate of claim 1 dissolved in the aqueous liquid.

18. The liquid composition of claim 5 wherein the liquid composition comprises at least 10 wt. % of the hydroxypropyl methyl cellulose phthalate of claim 1 dissolved in the aqueous liquid.

19. The hydroxypropyl methyl cellulose phthalate of claim 1 wherein the degree of neutralization of phthalyl groups is not more than 0.3.

20. The hydroxypropyl methyl cellulose phthalate of claim 1 wherein the degree of neutralization of phthalyl groups is not more than 0.1.

* * * * *